United States Patent [19]

Brun et al.

[11] Patent Number: 5,488,155
[45] Date of Patent: Jan. 30, 1996

[54] PREPARATION OF L-ASPARTIC ACID

[75] Inventors: Daniel Brun, Charly; Pierre-Yves Lahary, Lyons; Jean-Francois Thierry, Francheville, all of France

[73] Assignee: Rhone-Poulenc Chimie, Courbevoie Cedex, France

[21] Appl. No.: 456,375

[22] Filed: Jun. 1, 1995

Related U.S. Application Data

[63] Continuation of Ser. No. 120,751, Sep. 15, 1993, abandoned.

[30]  Foreign Application Priority Data

Sep. 15, 1992 [FR] France ................................ 92 10954

[51] Int. Cl.⁶ .................................................. C07C 227/00
[52] U.S. Cl. ............................ 562/554; 562/571; 435/109
[58] Field of Search .................................... 562/554, 571; 435/109

[56] References Cited

U.S. PATENT DOCUMENTS

| | | | |
|---|---|---|---|
| 4,013,508 | 3/1977 | Zangrandi | 195/28 |
| 4,560,653 | 12/1985 | Sherwin | 435/109 |
| 4,650,755 | 3/1987 | Wood | 435/43 |
| 4,732,851 | 3/1988 | Wood | 435/43 |
| 4,828,993 | 5/1989 | Sridhar | 435/136 |
| 5,093,253 | 3/1992 | Nolan | 435/178 |

FOREIGN PATENT DOCUMENTS

| | | |
|---|---|---|
| 0454126 | 10/1991 | European Pat. Off. . |
| 1004218 | 9/1965 | United Kingdom .................. 562/571 |
| 1200115 | 7/1970 | United Kingdom . |

OTHER PUBLICATIONS

Abstract of Japanese Patent No. 48056618 (1973).

*Primary Examiner*—Michael L. Shippen
*Attorney, Agent, or Firm*—Burns, Doane, Swecker & Mathis

[57] ABSTRACT

L-aspartic acid is improvedly prepared in high yields by treating ammonium aspartate, advantageously in aqueous reaction medium, with an effective, aspartic acid-precipitating amount of fumaric acid.

8 Claims, No Drawings

PREPARATION OF L-ASPARTIC ACID

This application is a continuation of application Ser. No. 08/120,751, filed Sep. 15, 1993, now abandoned.

BACKGROUND OF THE INVENTION

1. Field of the Invention

The present invention relates to a process for the preparation of L-aspartic acid.

2. Description of the Prior Art

Conventionally, L-aspartic acid is obtained from ammonium aspartate which itself is generally prepared via enzymatic treatment of ammonium fumarate. The precipitation of L-aspartic acid from ammonium aspartate is carried out using an inorganic or organic acid which has a $pK_a$ which is less than the corresponding acidity of L-aspartic acid, i.e., less than 3.65. Among the acids commonly used therefor, the inorganic acids are especially representative, more particularly sulfuric acid. Maleic acid can also be used.

However, in this type of precipitation, the production of the ammonium salt of the acid under consideration is observed jointly with the formation of the expected L-aspartic acid. With respect to L-aspartic acid, this byproduct constitutes an impurity which, indeed, must be removed. The corresponding separation stage is undesirable both on an economic level, because it requires additional cost in the process, and on an ecological level, by reason of contamination of effluents.

SUMMARY OF THE INVENTION

Accordingly, a major object of the present invention is the provision of improved means for efficiently and effectively precipitating L-aspartic acid from ammonium aspartate.

Briefly, the present invention features a process for the preparation of L-aspartic acid via ammonium aspartate, wherein the acid used to precipitate the aspartic acid from ammonium aspartate is fumaric acid.

DETAILED DESCRIPTION OF PREFERRED EMBODIMENTS OF THE INVENTION

More particularly according to the present invention, this ability of fumaric acid to efficiently precipitate L-aspartic acid from ammonium aspartate is indeed quite surprising and unexpected.

The two $pK_a$ values of fumaric acid are, in point of fact, not favorable for precipitating L-aspartic acid. The respective values of 3 and 4.4 are on the same order of magnitude as the corresponding $pK_a$ of L-aspartic acid.

Moreover, fumaric acid, in contrast to maleic acid, has a markedly lower solubility in aqueous mixture and at room temperature. The precipitation reaction is, therefore, in the presence of fumaric acid and over a wide temperature range, carried out in heterogeneous medium. However, such heterogeneity, unexpectedly, elicits no adverse effect on the excellent progression of the reaction.

In a preferred embodiment of the invention, fumaric acid is used in a molar ratio of added fumaric acid to ammonium aspartate present which is less than or equal to 0.8. Preferably, such molar ratio ranges from approximately 0.1 to 0.65.

The precipitation is conventionally carried out in an aqueous medium. The initial water concentration of the precipitation medium, before introduction of the fumaric acid, can vary widely. Generally, it ranges from approximately 40% to 90% by weight.

The reaction temperature is not a limiting factor to the extent that it remains compatible with L-aspartic acid. The precipitation can thus be carried out at room temperature or at 100° C., for example. Preferably, the reaction temperature is less than or equal to 100° C.

As indicated above, depending on the temperature selected, the precipitation reaction is carried out in homogeneous or heterogeneous medium. At approximately 100° C., it is a heterogeneous medium.

At the end of the reaction, the L-aspartic acid formed is isolated from the reaction mixture, preferably by filtration, washed and dried. In a specific embodiment of the invention, the filtrate containing the ammonium fumarate is retained.

The L-aspartic acid yield of the reaction can attain values of from 70% to 95%.

The present invention also features a process for the preparation of L-aspartic acid comprising, other than the stage of precipitation of L-aspartic acid with fumaric acid, the preliminary formation of ammonium aspartate from ammonium fumarate.

More precisely, the present invention also features the processes additionally comprising the preliminary production of ammonium aspartate by enzymatic treatment of ammonium fumarate with aspartases or microorganisms which produce aspartases.

The ability of aspartases to convert ammonium fumarate to aspartate is well known to this art and many techniques for producing aspartate by enzymatic treatment of aspartases with ammonium fumarate have to date been described in the literature. Consequently, these techniques will not here be repeated.

Microorganisms capable of producing aspartases include, especially, the following strains: *Pseudomonas fluorescens, Escherichia coli, Aerobacter aerogenes, Bacterium succinium,* Micrococcus sp., *Bacillus subtilis* and *Serratia marcescens.*

The ammonium aspartate obtained as a result of the enzymatic treatment is preferably isolated at the end of the reaction with a view to the subsequent precipitation stage with fumaric acid.

The use of fumaric acid for precipitating L-aspartic acid proves to be particularly advantageous in the second case. In effect, the byproduct obtained as a result of the precipitation stage, namely, ammonium fumarate, can advantageously constitute a source of L-aspartic acid. It can be recycled to prepare L-aspartic acid via the formation of ammonium aspartate and thus permits operation in a closed circuit. The formation of byproduct is then completely non-existent.

Consequently, according to a preferred embodiment of the invention, the reaction mixture, obtained as a result of the precipitation stage of aspartic acid and freed of said acid, is used as a source of ammonium fumarate for preparing ammonium aspartate.

This reaction mixture can be used directly, without any prior treatment, for preparing ammonium aspartate. From this viewpoint, microorganisms capable of producing aspartase are introduced directly therein with, if appropriate, readjustment of the ammonia stoichiometry.

In order to further illustrate the present invention and the advantages thereof, the following specific examples are given, it being understood that same are intended only as illustrative and in nowise limitative.

In said examples, the following tests were carried out:

The purity of the L-aspartic acid was monitored by potentiometric analysis (determination with 1N sodium hydroxide);

The amount of unreacted fumaric acid was also quantitatively determined by HPLC chromatography.

EXAMPLE 1

Preparation of ammonium aspartate:

300 g $NH_4OH$, containing 23.14% by weight of $NH_3$, and 800 g of water were introduced into a 2 l round-bottomed flask equipped with a magnetic stirrer. 543 g of L-aspartic acid were then added progressively such as to maintain the temperature of the mixture below 50° C. After cooling, a homogeneous 37.27% w/w ammonium aspartate aqueous solution was obtained.

EXAMPLE 2

Test No. 1 for precipitation of aspartic acid:

3.6 g of fumaric acid, with 25 g of water, were charged to a 100 ml Erlenmeyer flask. 25 g of the 37.27% w/w ammonium aspartate solution (0.0621 mol) of Example 1 were then added thereto. The water concentration in the mixture evaluated before reaction, without taking into account the fumaric acid present, C, was then 81.37% w/w and the molar ratio of added fumaric acid to ammonium aspartate present, $\alpha$, was 0.5.

The liquid/solid mixture was stirred using a magnetic stirrer for a time t=1 h at a temperature T=20° C. The suspension obtained was filtered and the L-aspartic acid recovered. After washing and drying, 67 g of a dry solid were obtained. The calculated L-aspartic acid yield, Y, was equal to 81.1 mol % (number of moles of L-aspartic acid obtained/number of moles of ammonium L-aspartate charged) and the calculated degree of conversion of the fumaric acid, D, was equal to 81.1% (number of moles of L-aspartic acid obtained/(2×(number of moles of fumaric acid charged)).

The purity of the L-aspartic acid obtained, determined by potentiometry, P, was 101.1% and the fumaric acid content, determined by HPLC, FA, was 1.8%.

EXAMPLE 3

Influence of temperature on the _precipitation of L-asapartic acid:

Test 2, presented below, was carried out under operating conditions analogous to those described in Example 2 (Test 1), but adjusting the reaction mixture to reflux at 100° C.

Test 3 was carried out according to the following protocol: 99.3 g of the 37.27% w/w ammonium aspartate solution (0.2467 mol) of Example 1, 90.7 g of water and 14.3 g of fumaric acid (0.1233 mol) were charged into a 300 ml stainless steel reactor equipped with a glass porthole which made it possible to observe the reaction mixture. The heating of the reactor was electrical and the stirring was provided by an Archimedean screw. After purging with nitrogen, the temperature was set at 135° C. and stirring was begun. After 15 minutes, the temperature of the reaction mixture reached 135° C. under autogenous pressure; the reaction mixture was then liquid and homogeneous. The temperature was maintained at 135°C. for 10 minutes. The reactor was then permitted to cool and discharge was carried out when the temperature of the reaction mixture reached 88° C.

The corresponding results Y, D, P and FA are presented in Table I below:

TABLE I

| TEST | T (°C.) | C (%) w/w | $\alpha$ | t | Y (%) | D (%) | P (%) | FA (%) |
|---|---|---|---|---|---|---|---|---|
| 1 | 20 | 81.37 | 0.5 | 1 h | 81.1 | 81.1 | 101.1 | 1.8 |
| 2 | 100 | 81.37 | 0.5 | 1.5 hr | 72 | 72 | 100.2 | 0.65 |
| 3 | 135 | 80.53 | 0.5 | 10 min | 62.5 | 62.5 | 100.7 | 1.1 |

The results evidence that it was the lowest temperatures which gave the best yields for satisfactory fumaric acid contents.

EXAMPLE 4

Influence of water concentration on the precipitation of aspartic acid:

This was studied at two temperature values, 20° C. and 100° C. The corresponding results are reported in Table II below.

Tests 4 and 5 were carried out in accordance with the procedure presented in Example 2 (Test 1).

As regards Test 6, it was carried out as follows: 25 g of the 37.27% w/w ammonium aspartate solution (0.0621 mol) of Example 1 were evaporated at 35° C. under a vacuum of 10 mm Hg in a rotary evaporator. 9.1 g of 48.77% w/w ammonium aspartate solution were then obtained. This solution was charged into a 50 ml Erlenmeyer flask. Stirring was provided using a magnetic stirrer. 3.6 g of fumaric acid were then added. The reaction mixture was then heated to reflux (temperature T=100° C).

TABLE II

| TEST | C (%) w/w | $\alpha$ | T (°C.) | t | Y (%) | D (%) | FA (%) |
|---|---|---|---|---|---|---|---|
| 4 | 81.37 | 0.3 | 20 | 1 h | 51.6 | 86 | 1.4 |
| 5 | 95.01 | 0.3 | 20 | 1 h | 28.1 | 46.8 | 0.7 |
| 6 | 51.23 | 0.5 | 100 | 1 h | 71 | 71 | 4.5 |
| 2 | 81.37 | 0.5 | 100 | 1.5 h | 72 | 72 | 0.65 |

At a very high water content, the yields diminished very significantly.

EXAMPLE 5

Influence of parameter $\alpha$ on the precipitation reaction;

The influence of the parameter $\alpha$ was studied at two temperature values, 20° C. and 100° C., in a manner identical to the preceding example.

Test 7 was carried cut according to the same procedure as Example 1 (Test 1).

Tests 8 and 9 were carried out according to the same procedure as Test 2, charging 0.0621 mol of ammonium aspartate. Test 10 was carried out at 140° C. according to the procedure described for Test 3, likewise charging 0.2467 mol of ammonium aspartate.

The results are reported in Table III below:

TABLE III

| TEST | $\alpha$ | C (%) w/w | T (°C.) | t | Y (%) | D (%) | FA (%) |
|---|---|---|---|---|---|---|---|
| 4 | 0.3 | 81.37 | 20 | 1 h | 51.6 | 86 | 1.4 |
| 1 | 0.5 | 81.37 | 20 | 1 h | 81.1 | 81.1 | 1.8 |
| 7 | 0.6 | 81.37 | 20 | 1 h | 87.4 | 72.9 | 3.5 |
| 2 | 0.5 | 81.37 | 100 | 1.5 h | 72 | 72 | 0.65 |
| 8 | 0.8 | 81.37 | 100 | 1.5 h | 88 | 55 | 10 |
| 9 | 1 | 81.37 | 100 | 3 h | 87 | 43.5 | 22 |

TABLE III-continued

| TEST | α | C (%) w/w | T (°C.) | t | Y (%) | D (%) | FA (%) |
|---|---|---|---|---|---|---|---|
| 10 | 1 | 80.53 | 140 | 10 min | 79 | 39.5 | 25 |

It was noted that, for a value of α greater than 0.8, the residual fumaric acid content became very high.

EXAMPLE 6

Precipitation of L-aspartic acid in the presence of ammonium fumarate:

1.79 g of fumaric acid, with 25 g of water, were charged into a 100 ml Erlenmeyer flask. 24.8 g of the 37.27% w/w ammonium aspartate solution (0.0617 mol) of Example 1 were then added thereto. The liquid/solid mixture was then stirred for 1 h at a temperature of 20° C. After filtering, washing and drying, 3.49 g of L-aspartic acid were obtained.

40.22 g of mother liquor were recovered after filtration and charged into a 100 ml Erlenmeyer flask. 8.78 g of the 37.27% ammonium aspartate solution of Example 1 and then 1.49 g of fumaric acid were added. The mixture was then stirred for 1 h at 20° C. After filtering, washing and drying, 3.05 g of L-aspartic acid were obtained. 37.59 g of the mother liquor were recovered after filtration and charged into a 100 ml Erlenmeyer flask. 7.3 g of the 37.27% w/w ammonium aspartate solution of Example 1 and then 1.18 g of fumaric acid were added. The mixture was then stirred for 1 h at 20° C. After filtering, washing and drying, 2.08 g of L-aspartic acid were obtained.

For the three stages, the molar ratio β of fumaric acid to ammonium aspartate, present at the beginning of reaction of the stage under consideration was also calculated, as well as the cumulative yield of the recycling stages, CY (number of moles of L-aspartic acid obtained up to the stage under consideration to number of moles of ammonium aspartate charged up to the stage under consideration).

The operating conditions α and β, as well as the results Y, CY and FA, are reported in Table IV below:

TABLE IV

| Stage | α | β | Y (%) | CY (%) | FA (%) |
|---|---|---|---|---|---|
| 1 | 0.25 | 0.25 | 42.6 | 42.6 | 0.6 |
| 2 | 0.25 | 0.294 | 44.6 | 61.2 | 0.8 |
| 3 | 0.25 | 0.321 | 38.4 | 67.2 | 1.5 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of L-aspartic acid, comprising treating ammonium aspartate with an effective,, aspartic acid-precipitating amount of fumaric acid in a heterogeneous reaction medium having solid fumaric acid present in the reaction medium at the outset of the treatment and at a temperature up to 100° C.

2. The process as defined by claim 1, wherein the molar ratio of fumaric acid to ammonium aspartate is no greater than 0.8.

3. The process as defined by claim 2, said molar ratio ranging from 0.1 to 0.65.

4. The process as defined by claim 1, carried out in an aqueous medium of precipitation.

5. The process as defined by claim 4, said aqueous medium of precipitation comprising from 40% to 90% by weight of water.

6. The process as defined by claim 1, comprising recovering said L-aspartic acid by filtration, washing and drying.

7. The process as defined by claim 1, comprising preparing said L-aspartic acid in a yield of at least 70%.

8. The process as defined by claim 1, comprising providing said ammonium aspartate by enzymatically treating ammonium fumarate with an aspartase or aspartase-producing microorganism.

* * * * *